(12) United States Patent
Otto et al.

(10) Patent No.: US 8,702,803 B2
(45) Date of Patent: Apr. 22, 2014

(54) LOCKING ASSEMBLY FOR TIBIAL PROSTHESIS COMPONENT

(75) Inventors: Jason Karl Otto, Plantation, FL (US); Ali Zafar Abbasi, Davie, FL (US)

(73) Assignee: Mako Surgical Corp., Fort Lauderdale, FL (US)

( * ) Notice: Subject to any disclaimer, the term of this patent is extended or adjusted under 35 U.S.C. 154(b) by 6 days.

(21) Appl. No.: 13/340,659

(22) Filed: Dec. 29, 2011

(65) Prior Publication Data

US 2013/0173011 A1 Jul. 4, 2013

(51) Int. Cl.
*A61F 2/38* (2006.01)

(52) U.S. Cl.
USPC ..................... 623/20.32; 623/20.28

(58) Field of Classification Search
USPC .......................... 623/20.28, 20.32
See application file for complete search history.

(56) References Cited

U.S. PATENT DOCUMENTS

| | | | |
|---|---|---|---|
| 4,711,639 A | 12/1987 | Grundei |
| 5,330,533 A | 7/1994 | Walker |
| 5,395,401 A | 3/1995 | Bahler |
| 5,609,639 A | 3/1997 | Walker |
| 6,210,445 B1 | 4/2001 | Zawadzki |
| 7,422,605 B2 | 9/2008 | Burstein et al. |
| 7,758,653 B2 | 7/2010 | Steinberg |
| D626,234 S | 10/2010 | Otto et al. |
| 7,842,092 B2 | 11/2010 | Otto et al. |
| 8,357,201 B2 | 1/2013 | Mayer et al. |
| 8,414,653 B2 | 4/2013 | Burstein et al. |
| 8,470,047 B2 | 6/2013 | Hazebrouck et al. |
| 8,475,535 B2 | 7/2013 | Otto |
| 2004/0034432 A1 | 2/2004 | Hughes et al. |
| 2010/0094429 A1 | 4/2010 | Otto |
| 2011/0066079 A1 | 3/2011 | Otto et al. |
| 2011/0082559 A1 | 4/2011 | Hartdegen et al. |
| 2012/0022658 A1 | 1/2012 | Wentorf |
| 2012/0035735 A1 | 2/2012 | Sanford et al. |
| 2013/0046385 A1 | 2/2013 | Hartdegen et al. |
| 2013/0184829 A1 | 7/2013 | Wyss et al. |
| 2013/0261758 A1 | 10/2013 | Claypool et al. |

FOREIGN PATENT DOCUMENTS

EP 2 428 188 3/2012

*Primary Examiner* — David H Willse
*Assistant Examiner* — Javier Blanco
(74) *Attorney, Agent, or Firm* — Foley & Lardner LLP (57) ABSTRACT

An orthopedic prosthetic system comprises a base portion and an elongated guide member protruding from a bottom surface of the base portion. The elongated guide member extends from a posterior edge of the base portion toward an anterior edge of the base portion and comprises an overhang element and an undercut face. The prosthetic system further comprises an insert portion configured to slideably engage the base portion and the elongated guide member. The insert portion comprises an underhang element configured to engage at least a portion of an undercut area defined by the overhang element and undercut face of the elongated guide member.

5 Claims, 5 Drawing Sheets

LOCKING ASSEMBLY FOR TIBIAL PROSTHESIS COMPONENT

TECHNICAL FIELD

The present disclosure relates generally to orthopedic prosthesis systems used in knee joint replacement surgeries and, more particularly, to a tibial prosthesis system having a locking assembly for securing a tibial insert portion of the tibial prosthesis to a tibial base portion of the tibial prosthesis.

BACKGROUND

The knee joint comprises the interface between the distal end of the femur and the proximal end of the tibia. In a properly-functioning knee joint, medial and lateral condyles of the femur pivot smoothly along menisci attached to respective medial and lateral condyles of the tibia. When the knee joint is damaged, the natural bones and cartilage that form the joint may be unable to properly articulate, which can lead to joint pain and, in some cases, interfere with normal use of the joint.

In some situations, surgery is required to restore normal use of the joint and reduce pain. Depending upon the severity of the damage, the surgery may involve partially or completely replacing the joint with prosthetic components. During such knee replacement procedures, a surgeon resects damaged portions of the bone and cartilage, while attempting to leave healthy tissue intact. The surgeon then fits the healthy tissue with artificial prosthetic components designed to replace the resected tissue and restore proper knee joint operation.

Some knee replacement procedures, such as total knee arthroplasty ("TKA"), involve the resection of some or all of each of the medial and lateral condyles of both the femur and tibia and the removal of the fibro-cartilage menisci located at the femorotibial interface. A prosthetic femoral component, typically made of titanium or other strong, surgical-grade metal, is fitted and secured to the distal end of the femur to replace the resected portion of the femur. Similarly, a prosthetic tibial component, the base of which is also typically made of titanium or other suitable metal, is fitted and secured to the proximal end of the tibia to replace the resected portion of the tibia.

The upper surface of the tibial component may include a flat or slightly concave element constructed of plastic material designed to replicate the form and function of the medial and lateral menisci located at the interface of the femur and tibia. This meniscus replacement element provides a low-friction surface upon which the femoral prosthesis can pivot smoothly at the femorotibial interface. The meniscus replacement element may be provided as part of a tibial prosthetic system, whereby a metallic tibial base component ("base" portion) is permanently secured to the tibia and the meniscus replacement element ("insert" portion) is subsequently inserted and secured to the tibial base component. Such a system allows for the insert portion to be replaced without disturbing the base portion if, for example, the insert portion becomes worn over time.

In an effort to reduce post-operative pain and shorten recovery times, surgeons continue to develop techniques for reducing the biological impact that many surgical procedures—including knee replacement procedures—have on the human body. Such techniques, which are commonly referred to as "minimally-invasive" techniques, are aimed at limiting the amount of tissue disturbance during the surgical procedure. For knee replacement surgery, this typically involves reducing the length of incision and limiting the amount of disturbance (e.g., cutting, stretching, etc.) of the muscles surrounding the knee joint.

Although minimally-invasive techniques may significantly reduce the amount of pain and recovery time endured by the patient, some of these techniques may limit the ability of the surgeon to visually inspect certain areas of the surgical site. For example, as the size of the incision used to perform a knee replacement procedure decreases, the surgeon's ability to visually inspect the posterior of the completed replacement joint may also decrease. Consequently, during minimally-invasive procedures, surgeons are increasingly reliant on non-visual (e.g., tactile) methods for ensuring that the tibial prosthesis components are installed properly. Incomplete or misaligned insertion of a component (e.g., tibial implant portion within the tibial base portion) can lead to discomfort and instability of the replacement joint, thereby increasing the likelihood of the necessity of subsequent corrective surgery.

In addition to the trend toward minimally-invasive surgical techniques, there is also a trend toward reducing manufacturing costs associated with prosthetic components. Decreasing manufacturing costs typically involves decreasing, at least to some degree, the precision with which the dimensions of the components match the specified design dimensions. In many orthopedic prosthetic systems, however, multiple components must precisely and firmly engage one another to limit movement between the components, increase stability, and reduce long-term wear. As a result, as lower cost, less precise manufacturing techniques are employed in the manufacture of prosthetic components, orthopedic prosthetic systems must be adapted to ensure that stability and function of the joint are not unduly compromised.

For example, in a tibial prosthetic implant system, manufacturing errors at the engagement interface between the tibial insert portion and the tibial base portion can result in movement or vibration of the insert component within the base component. This movement can cause micro-abrasions on the insert component that release small fragments of plastic into the knee joint. These fragments can cause significant irritation of the joint and/or lead to premature wear of the insert component. What is needed, therefore, is a solution for controlling manufacturing costs without sacrificing implant performance due to decreased precision of the implant components.

The presently disclosed locking assembly for a tibial base component is directed to overcoming one or more of the problems set forth above and/or other problems in the art.

SUMMARY

In accordance with one aspect, the present disclosure is directed to an orthopedic prosthetic system comprising a base portion and an elongated guide member protruding from a bottom surface of the base portion. The elongated guide member may extend from a posterior edge of the base portion toward an anterior edge of the base portion. The elongated guide member may comprise an overhang element and an undercut face. The orthopedic prosthetic system may also comprise an insert portion configured to slideably engage the base portion and the elongated guide member. The insert portion may comprise an underhang element configured to engage at least a portion of an undercut area defined by the overhang element and undercut face of the elongated guide member.

According to another aspect, the present disclosure is directed to an orthopedic prosthetic system comprising an insert portion configured to slideably engage a base portion.

The insert portion may comprise an underhang element configured to engage at least a portion of an undercut area defined by an overhang element of the base portion. The underhang element may comprise a stabilizer element having a different shape than the undercut area. The stabilizer element may be configured to substantially conform to the shape of the undercut area when the underhang element of the insert portion engages the base portion at the undercut area.

In accordance with another aspect, the present disclosure is directed to an orthopedic prosthetic system comprising a base portion having a first overhang element that extends inwardly from an outer edge of the base portion and defines a first undercut area. The base portion may also comprise an elongated guide member that protrudes from a bottom surface of the base portion and extends from a posterior edge of the base portion toward an anterior edge of the base portion. The elongated guide member may comprise a second overhang element and an undercut face, the second overhang element and the undercut face defining a second undercut area. The orthopedic prosthetic system may also comprise an insert portion configured to slideably engage the base portion. The insert portion may comprise a first underhang element configured to engage at least a portion of the first undercut area and a second underhang element configured to engage at least a portion of the second undercut area.

Additional objects and advantages will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the claims.

BRIEF DESCRIPTION OF THE DRAWINGS

The accompanying drawings, which are incorporated in and constitute a part of this specification, illustrate several embodiments that, together with the description, serve to explain the principles and features of the present disclosure.

DETAILED DESCRIPTION

Reference will now be made in detail to exemplary embodiments of the present disclosure, examples of which are illustrated in the accompanying drawings. Wherever possible, the same reference numbers will be used throughout the drawings to refer to the same or similar parts.

Figure 1:
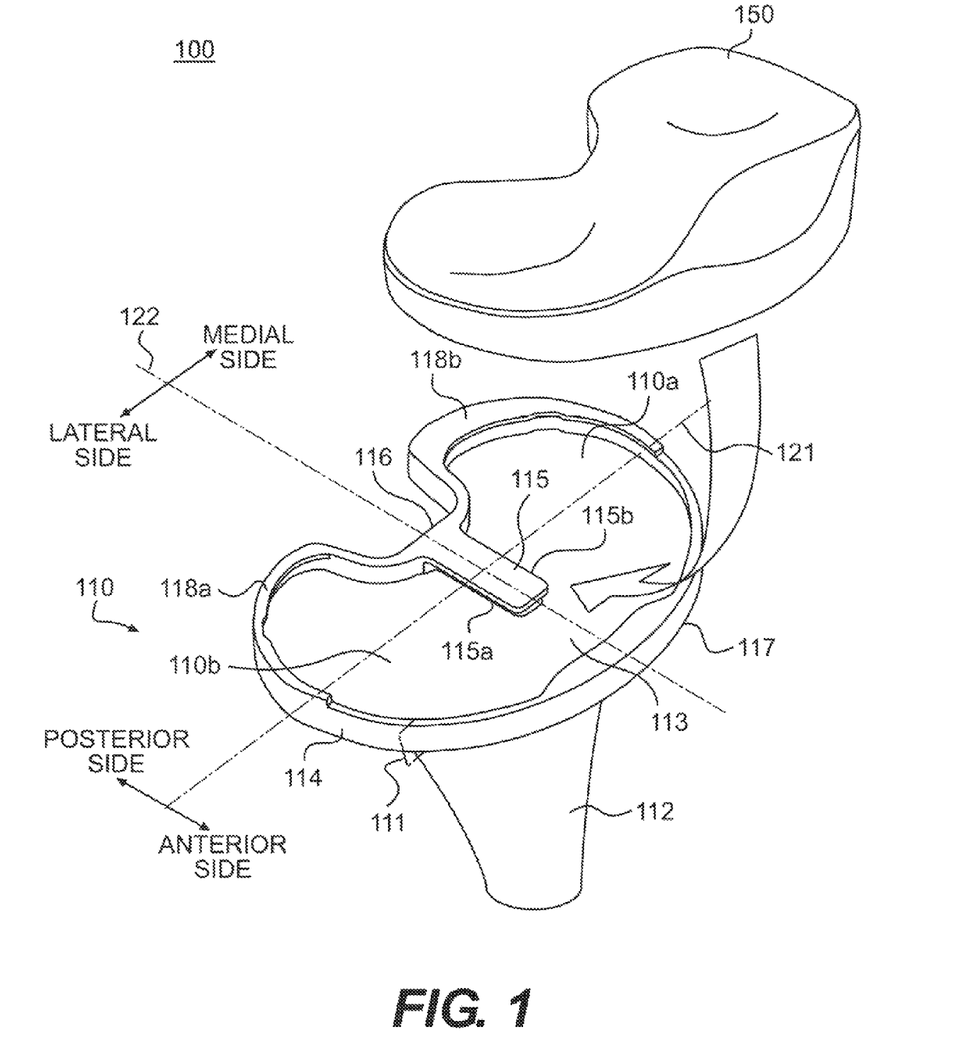
FIG. 1 illustrates a perspective view of a tibial prosthetic system comprising a base portion and an insert portion, consistent with certain disclosed embodiments.

FIG. 1 illustrates a perspective view of an exemplary tibial prosthetic system 100 that may be used in connection with a knee replacement or reconstructive procedure, such as total knee arthroplasty (TKA). In a TKA procedure, a surgeon attempts to restore proper function of the knee joint by resecting damaged portions of a patient's knee, and replacing the resected portions of the knee with prosthetic components. More specifically, the TKA procedure may involve removing and resurfacing the epicondyles at the distal end of the femur, and removing all or part of the proximal end of the tibia. The surgeon then replaces the removed femoral tissue with a femoral prosthetic component and the removed tibial tissue with a tibial prosthetic device, such as tibial prosthetic system 100.

Tibial prosthetic system 100 may include a plurality of components that may be configured to provide a stable surface that articulates with the femoral prosthetic (not shown) to restore proper knee joint function. As illustrated in FIG. 1, tibial prosthetic system 100 may include a base portion 110 and an insert portion 150. During a knee replacement procedure, base portion 110 may be secured to the proximal end of the tibia, which has been surgically prepared by removing damaged bone and tissue and reshaping the healthy bone to receive the base portion 110. Once base portion 110 is secured to the tibia, the surgeon completes assembly of tibial prosthetic system 100 by engaging and securing insert portion 150 to base portion 110.

As explained, base portion 110 may be secured to the proximal end of a surgically-prepared tibia and configured to emulate the structure and function of the top surface of the tibial bone. As such, base portion 110 may be manufactured from surgical-grade metal or metal alloy material (such as surgical-grade steel, titanium, etc.) that is substantially rigid for providing a stable base upon which to reconstruct the remainder of the prosthetic joint. Base portion 110 may comprise, among other things, a tray 111 and a stem 112.

Stem 112 may extend from an underside of tray 111 and may be any component suitable for fixing base portion 110 to the tibia. According to the embodiment shown in FIG. 1, stem 112 may embody a post that is configured to be inserted and cemented within the proximal end of the tibia. It is contemplated, however, that stem 112 may include additional and/or different features for securing base portion 110 to the tibia. For example, stem 111 may comprise one or more projections, keels, fasteners, spikes, biological in-growth structures, or any other component suitable for securing base portion 110 to the proximal end of the tibia.

Tray 111 may be coupled to a proximal end of stem 112. Tray 111 may comprise a bottom surface 113 (or "floor") that is designed to have a size and shape similar to the natural tibia of a patient. Tray 111 may also comprise a sidewall 114 that extends vertically from the peripheral edge that surrounds bottom surface 113. Sidewall 114, together with bottom surface 113, form a well configured to receive insert portion 150.

Base portion 110 may include a plurality of features that are designed to contribute to proper alignment and/or engagement of insert potion 150 with base portion 110. For example, base portion 110 may include one or more overhang elements 118a-118c. Overhang elements 118a-118c may be integrally formed at the top edge of sidewall 114 and may extend inwardly, toward the center of base portion 110. The inward extension of overhang elements 118a-118c, together with the inner surface of sidewall 114, form undercut areas (120a, 120b, shown in detail in FIG. 3B) that are configured to engage corresponding underhang elements (151a-151c, shown in greater detail in FIG. 4) of insert portion 150. Overhang elements 118a-118c may be configured to limit the vertical movement of insert portion 150 when corresponding underhang elements of insert portion 150 are engaged and secured beneath overhang elements 118a-118c.

Base portion 110 may also comprise a guide member 115 that protrudes from bottom surface 113 of base portion 110 and extends from a posterior edge 116 toward an anterior edge 117 of base portion 110. According to the exemplary embodiment illustrated in FIG. 1, guide member 115 may bisect base portion 110 substantially along a medial/lateral axis 122. As such, guide member 115 may separate base portion 110 into medial and lateral guide zones 110a, 110b, respectively. Guide member 115 may comprise one or more overhang elements 115a, 115b that extend outwardly from a centerline of guide member 115. Guide member 115 may also comprise one or more undercut faces (115c, 115d, shown in detail in FIG. 3A) that, together with overhang elements 115a, 115b, define undercut areas (120d, 120e, shown in detail in FIG. 3A).

According to one exemplary embodiment, guide member 115 may be elongated, extending past an anterior/posterior midline 121 of base portion 110. The length of guide member 115 illustrated in the exemplary embodiment of FIG. 1 is configured to ensure that insert portion 150 is precisely positioned and aligned with base portion 110 along a majority of the length of base portion 110. By extending along a significant portion of the length of base portion 110, guide member 115 is configured such that insert portion 150 is precisely aligned with base portion 110 along a desired medial-lateral axis 122 well before the insert portion 150 is vertically aligned with base portion 110 and set within tray 111. Such a system enables a surgeon to first focus on aligning insert portion 150 and base portion 110 along a medial/lateral axis while insert portion 150 is relatively close to an anterior edge of base portion 110 (where visibility and maneuverability at the surgical site is greatest). Once aligned, guide member 115 is configured to ensure that alignment is maintained until insert portion 150 is fully engaged with base portion 110. This is particularly advantageous in minimally-invasive surgical procedures, where it may be difficult for a surgeon to visibly determine when an insert portion 150 is properly aligned with base portion 110 toward the back of the knee joint.

Figure 2:
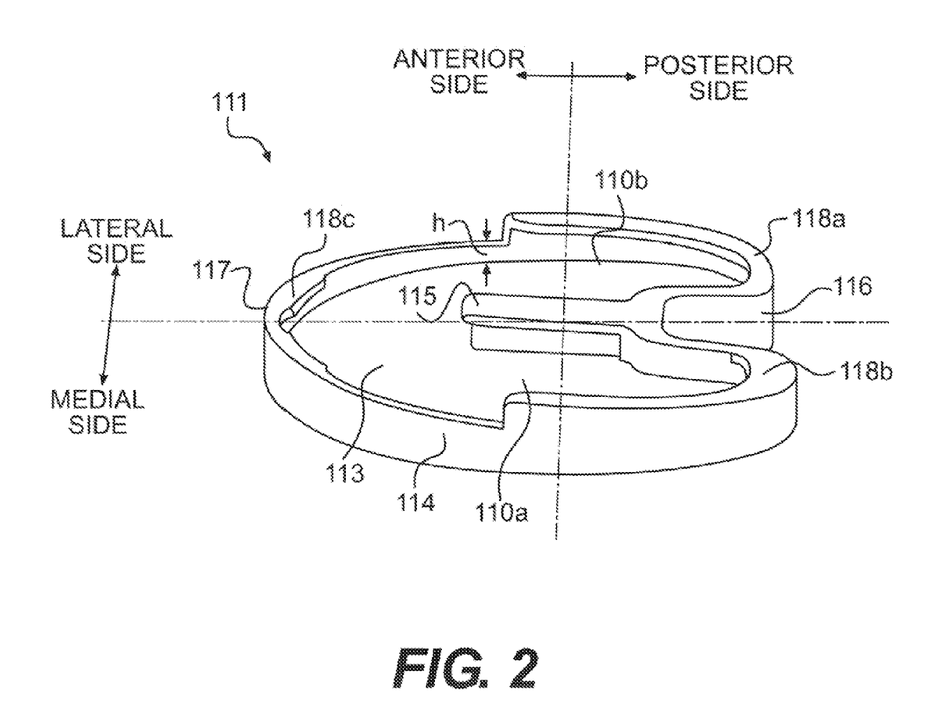
FIG. 2 illustrates a perspective view of a base portion of a tibial prosthetic system, in accordance with an exemplary disclosed embodiment.

FIG. 2 provides a perspective side view of tray 111 of base portion 110 in accordance with certain disclosed embodiments. Tray 111 may comprise height, h, that is measured from bottom surface 113 of base portion 110 to the underside of overhang elements 118a-118c. According to one embodiment, tray 111 may be angled, such that the height toward the anterior edge 117 of base portion 110 is greater than the height toward the posterior edge 116 of base portion 110. This difference in height defines medial and lateral guide zones 110a, 110b with substantially angled profiles. These angled profiles provide an additional mechanism for ensuring that insert portion 150 is initially aligned along a desired medial-lateral axis 122, and that such alignment is maintained substantially over the length of base portion 110 as the insert portion 150 is engaged with base portion 110. Furthermore, angled guide zones 110a, 110b may encourage the surgeon to apply a substantially equal amount of force to medial and lateral sides of insert portion 150 while sliding insert portion 150 along guide member 115.

Figure 3A:
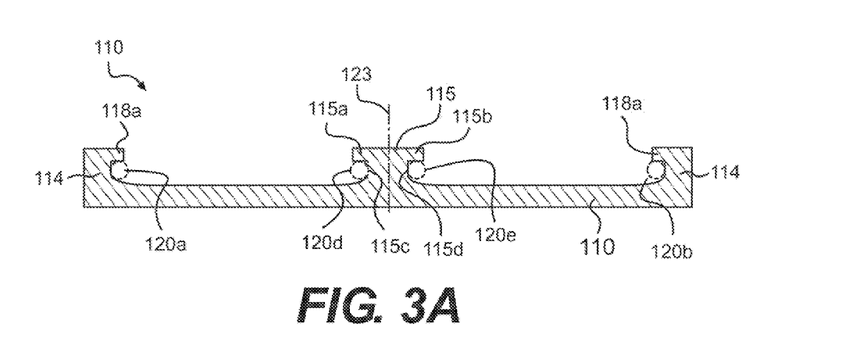
FIG. 3A provides a cross section view of an assembled tibial prosthetic system, consistent with certain exemplary disclosed embodiments.

FIG. 3A provides a cross section view of base portion 110, consistent with certain exemplary embodiments. As illustrated in FIG. 3A, overhang elements 118a, 118b may extend from the top of sidewall 114 toward the center of base portion 110, thereby defining undercut areas 120a, 120b, respectively. According to one embodiment, underside edges of overhang elements 118a, 118b intersect the inner surface of a corresponding sidewall 114 angles of approximately 90°. It should be noted, however, that lower edges of the overhang elements 118a, 118b may intersect the inner surface of a corresponding sidewall 114 at angles slightly greater or less than 90°.

Similarly, overhang elements 115a, 115b of guide member 115 may outwardly from a center 123 of guide member 115, thereby defining undercut areas 120d, 120e, respectively. According to one embodiment, lower edges of the overhang elements 115a, 115b intersect respective undercut faces 115c, 115d of guide member 115 at angles of approximately 90°. It should be noted, however, that lower edges of the overhang elements 115a, 115b may intersect respective undercut faces 115c, 115d of guide member 115 at angles slightly greater or less than 90°.

According to other exemplary embodiments, overhang elements 115a, 115b of guide member 115 may intersect undercut faces 115c, 115d of guide member at angles of between 1 and 45°, thereby forming a dovetail guide feature for gradually guiding insert portion 150 into base portion 110. According to certain embodiments the angle of intersection may be between 30° and 45°, with an exemplary embodiment being approximately 30°.

Figure 3B:
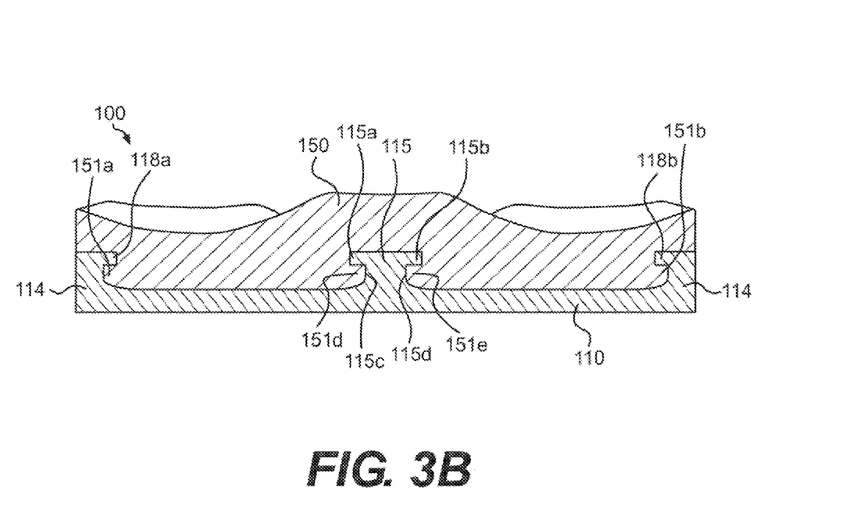
FIG. 3B provides a cross section view of a guide member, in accordance with an exemplary embodiment of the disclosure.

FIG. 3B provides a cross section view of a fully assembled prosthetic system 100 in accordance with certain disclosed embodiments. As illustrated in the exemplary embodiment of FIG. 3A, underhang elements 151a, 151b of insert portion 150 may be configured to engage overhang elements 118a, 118b, respectively, of base portion 110. Alternatively or additionally, underhang elements 151d, 151e of insert portion 150 may be configured to engage with overhang elements 115a, 115b of guiding island 115.

In accordance with certain embodiments described above, guide member 115 of tibial prosthetic system 100 is configured to ensure that insert portion 150 is aligned with base portion 110 early in the insert engagement process, and that proper alignment is maintained as insert portion 150 is guided along the length of guide member 115 until insert portion 150 reaches the posterior edge 116 of base portion 110. According to certain other embodiments described above, base portion 110 includes a plurality of angled medial and lateral guide zones 110a, 110b, which are configured to ensure that insert portion 150 engages base portion 110 in a direction consistent with the angled profile. As an alternative or in addition to the embodiments described above for ensuring proper alignment and engagement of insert portion 150 with base portion 110, features consistent with the present embodiments provide solutions for limiting movement of insert portion 150 within tray 111 of base portion 110 after insert portion 150 is set within base portion 110. FIGS. 4 and 5A-5C illustrate such exemplary embodiments for limiting movement of insert portion 150 relative to base portion 110.

Figure 4:
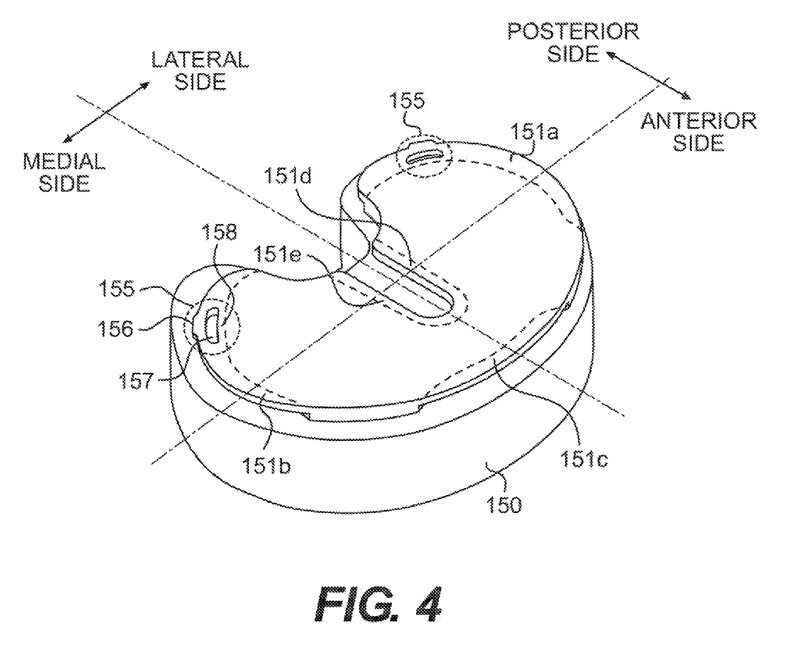
FIG. 4 provides a bottom view of an insert portion of a tibial prosthetic system comprising an exemplary stabilizer element, consistent with the disclosed embodiments.

FIG. 4 provides a perspective view of the underside of insert portion 150. Insert portion 150 may be designed to emulate the form and function of certain components of the natural femorotibial interface, including, among other things, medial and lateral menisci of the knee joint. As such, insert portion 150 may be constructed of smooth, semi-rigid synthetic or semi-synthetic plastic, rubber, or polymer material. Insert portion 150 may be configured to provide a smooth surface that is designed to articulate with a femoral implant component during normal knee operation. As will be explained in greater detail below, insert portion 150 is configured to removably engage with base portion 110. Accordingly, insert portion 150 is configured for periodic replacement if insert portion 150 deteriorates over time due, for example, to excessive wear.

As shown in FIG. 4 and as described above, insert portion 150 may comprise a plurality of underhang elements 151a-151c arranged along the peripheral edges of insert portion 150. Underhang elements 151a-151c may be configured to engage with corresponding undercut areas 120 defined by overhang elements 118a-118c of base portion 110. Insert portions 150 may also comprise one or more undercut areas 151d, 151e situated toward the center of insert portion 150 and defining a female component configured to engage the male portion define by guide member 115. Underhang elements 151d, 151e may be configured to engage with corresponding undercut areas 120d, 120e defined by overhang elements 115a, 115b of guide member 115. As explained, the disclosed interaction of underhang elements of insert portion 150 with overhang elements of base portion 110 provides a system for initially aligning insert portion 150 with base portion 110, maintaining uniform alignment during the process of engaging of insert portion 150 with base portion 110, and securing insert portion 150 with base portion 110 so as to limit the vertical movement (and/or vibration) of insert portion 150 with respect to base portion 110 during operation of the knee joint. Furthermore, because certain disclosed embodiments employ an elongated guide member 115 that protrudes from a bottom surface 113 of base portion 110 along a majority of the length of base portion 110 (in an anterior-posterior direction), alignment of insert portion 150 with base portion 110 may be reliably maintained during the engagement process, without requiring significant additional repositioning or realignment by the surgeon.

As illustrated in FIG. 4, insert portion 150 may comprise one or more stabilizing elements 155. According to one embodiment, stabilizing element 155 may be integrally formed as part of insert portion 150 and may be configured to substantially conform to the shape of a corresponding section of base portion 110 when insert portion 150 engages base portion 110. For example, as illustrated in FIG. 4, stabilizing element 155 may be integrally formed as part of underhang element 151b and may comprise a projection 156 that extends outwardly from an edge of underhang element 151b. Stabilizing element 155 may also comprise a void 157 disposed substantially between projection 156 and an internal section 158 of stabilizing element 155. As underhang element 151b is engaged with undercut area 120b, projection 156 contacts sidewall 114 of base portion 110. As underhang element 151b begins to engage sidewall 114, projection 156 begins to deform inwardly toward void 157. However, because projection 156 is made of semi-rigid material, it exerts a persistent force against sidewall 114 of base portion 110 while insert portion 150 is engaged with base portion 110. This persistent force may urge insert portion 150 against an opposing edge of base portion 110. For example, when disposed toward a posterior edge of insert portion 150, stabilizing element 155 may urge insert portion against an anterior edge of base portion 110. Accordingly, the persistent force provided by stabilizing element 155 may limit and/or inhibit the amount of lateral movement of insert portion 150 within tray 111 of base portion 110. This, in turn, may reduce wear of insert portion 110 caused by friction between insert portion 150 and base portion 110.

According to the embodiment illustrated in FIG. 4, void 157 may comprise an area that embodies a discontinuity between projection 156 and a corresponding internal section 158 of stabilizing element 155. According to one embodiment, this discontinuity may be occupied by air or other material that substantially surrounds void 157. It is contemplated, however, that this discontinuity may comprise other materials. For example, void 157 may be filled with neoprene or other material that is substantially more compressible than the material used to construct insert portion 150. Not only would such material ensure that void 157 does not become filled with foreign matter that may obstruct the proper function of stabilizing element 155, it may also decrease the amount by which projection 156 deforms, thereby potentially enhancing the stabilizing force provided by stabilizing element 155.

As an alternative or in addition to stabilizing element(s) 155 illustrated in embodiments consistent with FIG. 4, insert portion 150 may include additional and/or different features for limiting the amount of lateral movement of insert portion 150 within base portion 110. As illustrated in the embodiments shown in FIGS. 5A-5C, stabilizing element(s) 155 may embody a portion of underhang element 151a of insert portion 150 that has a substantially different shape (in an uninserted state, shown on the left) than a corresponding undercut portion of base portion 110. Stabilizing elements 155, such as those illustrated in the embodiments shown in FIGS. 5A-5C, may be configured to substantially conform to a shape of a corresponding section of base portion 110 when insert portion 150 is engaged with base portion 110 (in an inserted state, shown on the right), thereby exerting a stabilizing force against base portion 110.

Figure 5A:
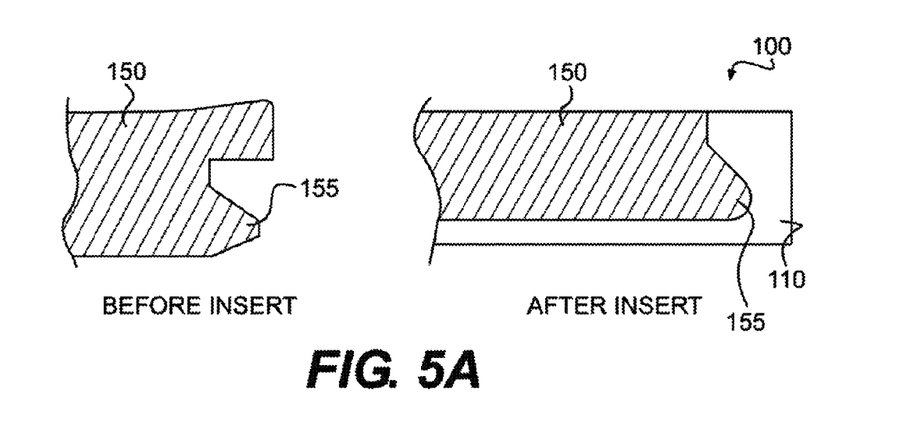
FIGS. 5A-5C provide respective cross-section views of exemplary stabilizer elements of an insert portion of a tibial prosthetic system, in accordance with certain disclosed embodiments.
Figure 5B:
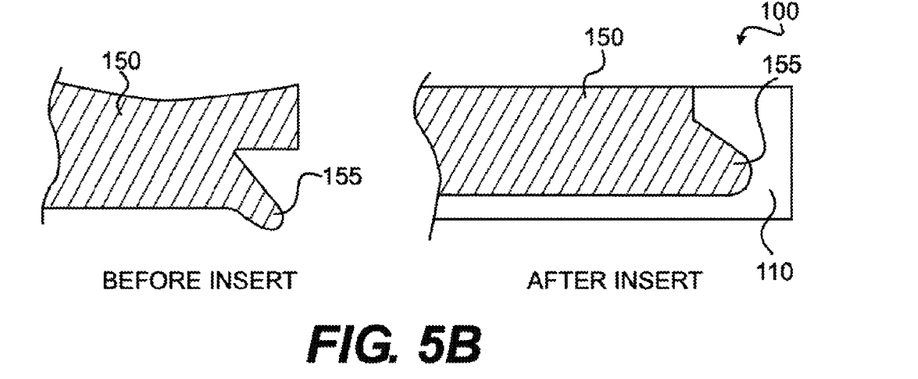
Figure 5C:
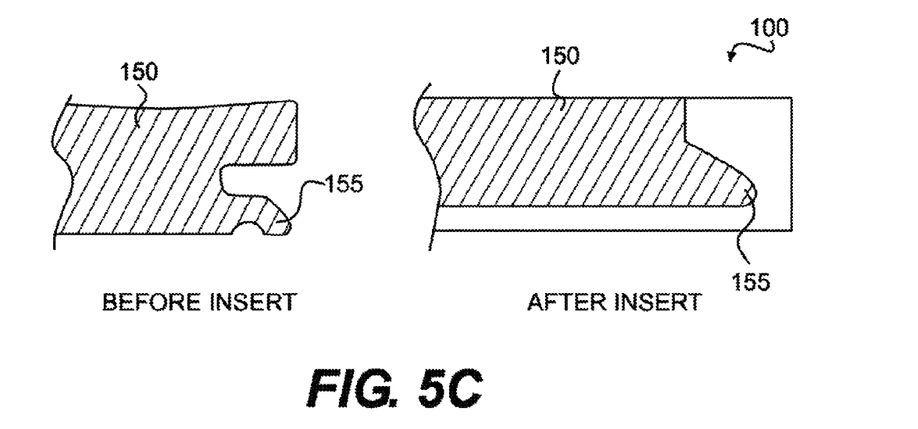

It is contemplated that stabilizing elements 155 consistent with the embodiments illustrated in FIGS. 5A-5C may be located in a substantially isolated section of underhang element 151a, similar to the size of the section occupied by stabilizing element 155 of FIG. 4. Alternatively, stabilizing elements 155 illustrated in FIGS. 5A-5C may comprise the majority of peripheral edge(s) of underhang elements 151a, 151b. Those skilled in the art will recognize that the stabilizing force provided by stabilizing element 155 is proportional to the length (or size) of stabilizing element 155. Furthermore, for stabilizing elements consistent with the embodiments shown in FIGS. 5A-5C, the amount of stabilizing force may be defined, at least in part, by the amount of difference between the shape of the stabilizing element and the shape of base portion 110. Stated another way, the stabilizing force of stabilizing elements 155 may be proportional to the amount of deformation of the stabilizing element when engaged with base portion 110.

It is contemplated that the embodiments described herein for aligning, securing, and stabilizing insert portion 150 with respect to base portion 110 may each be configured to operate alone or in combination with one or more of the other embodiments described herein. For example, it is contemplated that the stabilizing features illustrated in FIG. 4 may be configured to operate alone or in combination with one or more of the stabilizing features illustrated in FIGS. 5A-5C. Alternatively or additionally, the stabilizing features illustrated in FIGS. 5A-5C may be configured to operate alone or in combination with the features of guide member 115 described and illustrated with respect to FIGS. 1-3.

The systems and features described herein provide a solution that allows a surgeon to initially align an insert portion with a base portion, while the insert portion is positioned relatively closely to an anterior edge of the tibial implant. Once initially aligned, the insert portion may be slideably engaged with the base portion. During engagement, guide member 115 substantially maintains the alignment of insert portion relative to base portion without requiring significant effort by the surgeon to maintain such alignment. This may be particularly advantageous in environments where a surgeon's visibility and ability to maneuver the insert is significantly impaired toward the posterior of the surgical site, such as during a minimally-invasive procedure where only a relatively limited area is accessible by the surgeon.

Furthermore, the elongated guide element consistent with certain disclosed embodiments is integrally formed with and protrudes from the bottom surface of the base portion along a significant percentage of the length of the base portion. Thus, unlike certain conventional prosthetic systems that only provide overhang tabs that extend along the posterior wall of the base portion (thereby allowing significant opportunity for misalignment as the insert portion travels toward the rear of the base portion), the presently disclosed prosthetic system limits the opportunity for misalignment as the insert portion is engaged with base portion.

In addition to providing a mechanism for reliably aligning and guiding the insert portion as it is engaged with a base portion of a tibial prosthetic system, the presently disclosed embodiments provide a solution for securing the insert portion within the base portion, while limiting the amount of movement of the insert portion with respect to the base portion. Specifically, by providing an elongated guide member that traverses the center of base portion 110, the presently disclosed prosthetic system increases the surface area dedicated to securing the insert portion to the base portion, particularly when compared with prosthetic systems having tabs only at the periphery of the implant.

Similarly, by providing one or more stabilizing elements that are integrally formed as part of underhang elements of the tibial insert portion, the prosthetic system described herein provides a self-contained mechanism for limiting lateral movement of the insert portion relative to the base portion. Such stabilizing elements may limit the amount of abrasive wear caused by friction due to movement at the insert/base interface, thereby increasing the durability of the insert portion and reducing the need for potentially costly and painful surgery to replace the insert portion. These integrated stabilizing elements may also limit the need for foreign objects, such as screws, clips, or fasteners to restrict movement of the insert portion relative to the base portion.

It will be apparent to those skilled in the art that various modifications and variations can be made to the disclosed systems for aligning and securing a tibial insert portion of a tibial prosthesis to a tibial base portion of the tibial prosthesis. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A tibial prosthetic system comprising:
 a tibial base portion configured to be secured to the proximal end of a surgically-prepared tibia, the tibial base portion comprising:
  a sidewall extending vertically from a peripheral edge that surrounds a bottom surface of the base portion;
  a first overhang element that extends inwardly from a top edge of the sidewall and defines a first undercut area; and
  an elongated guide member upwardly protruding from said bottom surface of the base portion and extending from a posterior edge of the base portion toward an anterior edge of the base portion, the elongated guide member comprising a second overhang element and an undercut face, the second overhang element and the undercut face defining a second undercut area; and
 a tibial insert portion configured to slideably engage the base portion and comprising:
  a first underhang element configured to directly engage at least a portion of the first undercut area; and
  a second underhang element configured to directly engage at least a portion of the second undercut area,
 wherein the first underhang element of the insert portion comprises a stabilizer element having a different shape than the first undercut area such that the stabilizer element substantially deforms and conforms to the shape of the first undercut area when the first underhang element of the insert portion engages with the base portion at the first undercut area.

2. The prosthetic system of claim 1, wherein a lower edge of the second overhang element intersects the undercut face of the elongated guide member at an angle of approximately 90°.

3. The prosthetic system of claim 1, wherein the stabilizer element is integrally formed as part of the insert portion.

4. The prosthetic system of claim 1, wherein the elongated guide member extends past an anterior-posterior midpoint of the base portion.

5. The prosthetic system of claim 1, wherein the elongated guide member comprises a length in an anterior-posterior direction that is greater than a width in a medial-lateral direction.

* * * * *